(12) United States Patent
Greener et al.

(10) Patent No.: US 7,148,339 B2
(45) Date of Patent: Dec. 12, 2006

(54) TEMPERATURE SENSITIVE MUTANT OF BACTERIOPHAGE T4 ENDONUCLEASE VII

(75) Inventors: Alan L. Greener, San Diego, CA (US); Lisa Joy Hexdall, San Diego, CA (US); Carsten Peter Carstens, San Diego, CA (US); Joseph A. Sorge, Del Mar, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 11/088,322

(22) Filed: Mar. 23, 2005

(65) Prior Publication Data

US 2005/0186676 A1  Aug. 25, 2005

Related U.S. Application Data

(63) Continuation of application No. 10/246,838, filed on Sep. 19, 2002, now abandoned, which is a continuation-in-part of application No. 10/180,174, filed on Jun. 26, 2002, now abandoned.

(51) Int. Cl.
*C07H 21/04* (2006.01)
*C12N 1/21* (2006.01)

(52) U.S. Cl. .................. 536/23.2; 536/23.1; 435/252.3

(58) Field of Classification Search ..................... None
See application file for complete search history.

(56) References Cited

U.S. PATENT DOCUMENTS

| | | | | |
|---|---|---|---|---|
| 5,698,400 | A | 12/1997 | Cotton et al. | 435/6 |
| 5,824,471 | A | 10/1998 | Mashal et al. | 435/6 |
| 5,824,530 | A * | 10/1998 | Kemper et al. | 435/199 |
| 5,876,941 | A | 3/1999 | Landegren et al. | 435/6 |
| 5,888,732 | A | 3/1999 | Hartley et al. | 435/6 |
| 5,958,692 | A | 9/1999 | Cotton et al. | 435/6 |
| 6,174,678 | B1 * | 1/2001 | Menzel et al. | 435/6 |
| 2002/0088021 | A1 * | 7/2002 | Mahajan | 800/278 |

OTHER PUBLICATIONS

Thompson et al. Heteroduplexes in mixed-template amplifications: formation, consequence and elimination by 'reconditioning PCR'. Nucleic Acids Research, vol. 30, No. 9, pp. 2083-2088, May 2002.*
Golz et al. Identification of amino acids of endonuclease VII essential for binding and cleavage of cruciform DNA. Eur. J. Biochem. vol. 245, pp. 573-580, 1997.*
Raaijmakers et al. X-ray structure of T4 endonuclease VII: a DNA junction resolvase with a novel forkd and unusual domain-swapped dimer architecture. The EMBO Journal., vol. 18, No. 6, pp. 1447-1458, 1999.*
Surdi, G. et al., "Discrimination of DNA duplexes with matched and mismatched tandem repeats by T4 endonuclease VII", (1999), *Genetic Analysis:Biomolec. Eng.*, 14:177-179.
Youil, R. et al., "Detection of 81 of 81 Known Mouse β-Globin Promoter Mutations with T4 Endonuclease VII-The EMC Method", (1996), *Genomics*,. 32:431-435.
Raaijmakers, H. et al., "Conformational Flexibility in T4 Endonuclease VII Revealed by Crystallography: Implications for Substrate Binding and Cleavage", (2001), *J. Mol. Biol.*, 308:311-323.
Hartung, M. et al., "Analyses of spontaneous mutations of cloned gene 49 of phage T4", (2001), *Mutation Research*, 473:201-210.
Golz, S. et al., "Enzymatic mutation detection. Procedure for screening and mapping of mutations by immobilised endonuclease VII", (1998), *Nucleic Acids Res.*, 26(4):1132-1133.
Giraud-Panis, M.E. et al., "T4 Endonuclease VII—a zinc containing four-way DNA junction resolving enzyme", (1997), *Bioch. Soc. Trans.*, 25:110.
Giraud-Panis, M.E. et al., "Near-simultaneous DNA cleavage by the subunits of the junction-resolving enzyme T4 endonuclease VII", (1997), *EMBO Journal*, 16(9):2528-2534.
Birkenbihl, R.P. et al., "Localization and Characterization of the Dimerization Domain of Holliday Structure Resolving Endonuclease VII of Phage T4", (1998), *J. Mol. Biol.*, 280:73-83.
Babon, J.J. et al., "The Use of Resolvases T4 Endonuclease VII and T7 Endonuclease I in Mutation Detection", (2000); *Methods in Molecular Biology*, 152:187-199.
Babon, J.J. et al., "Mutation detection using fluorescent enzyme mismatch cleavage with T4 endonuclease VII", (1999), *Electrophoresis*, 20:1162-1170.
Golz, S. et al., "Enzymatic mutation detection: enrichment of heteroduplexes from hybrid DNA mixtures by cleavage-deficient GST-tagged endonuclease VII", (1999), *Nucleic Acids Research*, 27(15):e7-i-iv.
International Search Report for International Application No. PCT/US03/19575 dated Dec. 1, 2003.

* cited by examiner

*Primary Examiner*—Celine Qian
*Assistant Examiner*—Jennifer Dunston
(74) *Attorney, Agent, or Firm*—Kathleen M. Williams; Mark J. FitzGerald; Edwards Angell Palmer & Dodge LLP

(57) ABSTRACT

The subject invention provides for a method of selectively cloning homoduplex nucleic acid molecules, in particular, by using a strain of host cells that contains a conditionally expressed and/or conditionally active mismatch-recognizing enzyme, e.g., a temperature sensitive variant of the gene encoding the endonuclease VII from phage T4. Using this host strain, the invention features a novel cloning method that selects for PCR products that are devoid of PCR-generated mutations.

4 Claims, 6 Drawing Sheets

Temperature Sensitive mutant T4 endonuclease VII nucleic acid sequence (SEQ ID NO:1) and amino acid sequence (SEQ ID NO:2)

```
atg tta ttg act ggc aaa tta tac aaa gaa gaa aaa cag aaa ttt tat      48
Met Leu Leu Thr Gly Lys Leu Tyr Lys Glu Glu Lys Gln Lys Phe Tyr      16 gat gca caa aac ggt aaa tgc tta att tgc caa cga gaa cta aat cct      96
Asp Ala Gln Asn Gly Lys Cys Leu Ile Cys Gln Arg Glu Leu Asn Pro      32 gat gtt caa gct aat cac ctc gac cat gac cat gaa tta aat gga cca     144
Asp Val Gln Ala Asn His Leu Asp His Asp His Glu Leu Asn Gly Pro      48 aaa gca gga aag gtg cgt gga ttg ctt tgt aat cta tgc aat gct gca     192
Lys Ala Gly Lys Val Arg Gly Leu Leu Cys Asn Leu Cys Asn Ala Ala      64 gaa ggt caa atg aag cat aaa ttt aat cgt tct ggc tta aag gga caa     240
Glu Gly Gln Met Lys His Lys Phe Asn Arg Ser Gly Leu Lys Gly Gln      80 ggt gtt gat tat ctt gaa tgg tta gaa aat tta ctt act tat tta aaa     288
Gly Val Asp Tyr Leu Glu Trp Leu Glu Asn Leu Leu Thr Tyr Leu Lys      96 tcc gat tac acc caa aat aat att cac cct aac ttt gtt gga gat aaa     336
Ser Asp Tyr Thr Gln Asn Asn Ile His Pro Asn Phe Val Gly Asp Lys     112 tca aag gaa ttt tct cgt tta gga aaa gag gaa atg atg gcc gag atg     384
Ser Lys Glu Phe Ser Arg Leu Gly Lys Glu Glu Met Met Ala Glu Met     128 ctt caa aga gga ttt gaa tat aat gaa tct gac acc aaa aca caa tta     432
Leu Gln Arg Gly Phe Glu Tyr Asn Glu Ser Asp Thr Lys Thr Gln Leu     144 ata gct tca ttc aag aag cag ctt aga aga gtt taa aat ga              473
Ile Ala Ser Phe Lys Lys Gln Leu Arg Arg Val                         155
```

Fig. 1

Wild Type T4 endonuclease VII nucleic acid sequence (SEQ ID NO:3) and
amino acid sequence (SEQ ID NO:4)

```
atg tta ttg act ggc aaa tta tac aaa gaa gaa aaa cag aaa ttt tat     48
Met Leu Leu Thr Gly Lys Leu Tyr Lys Glu Glu Lys Gln Lys Phe Tyr     16 gat gca caa aac ggt aaa tgc tta att tgc caa cga gaa cta aat cct     96
Asp Ala Gln Asn Gly Lys Cys Leu Ile Cys Gln Arg Glu Leu Asn Pro     32 gat gtt caa gct aat cac ctc gac cat gac cat gaa tta aat gga cca    144
Asp Val Gln Ala Asn His Leu Asp His Asp His Glu Leu Asn Gly Pro     48 aaa gca gga aag gtg cgt gga ttg ctt tgt aat cta tgc aat gct gca    192
Lys Ala Gly Lys Val Arg Gly Leu Leu Cys Asn Leu Cys Asn Ala Ala     64 gaa ggt caa atg aag cat aaa ttt aat cgt tct ggc tta aag gga caa    240
Glu Gly Gln Met Lys His Lys Phe Asn Arg Ser Gly Leu Lys Gly Gln     80 ggt gtt gat tat ctt gaa tgg tta gaa aat tta ctt act tat tta aaa    288
Gly Val Asp Tyr Leu Glu Trp Leu Glu Asn Leu Leu Thr Tyr Leu Lys     96 tcc gat tac acc caa aat aat att cac cct aac ttt gtt gga gat aaa    336
Ser Asp Tyr Thr Gln Asn Asn Ile His Pro Asn Phe Val Gly Asp Lys    112 tca aag gaa ttt tct cgt tta gga aaa gag gaa atg atg gcc gag atg    384
Ser Lys Glu Phe Ser Arg Leu Gly Lys Glu Glu Met Met Ala Glu Met    128 ctt caa aga gga ttt gaa tat aat gaa tct gac acc aaa aca caa tta    432
Leu Gln Arg Gly Phe Glu Tyr Asn Glu Ser Asp Thr Lys Thr Gln Leu    144 ata gct tca ttc aag aag cag ctt aga aag agt tta aaa tga            474
Ile Ala Ser Phe Lys Lys Gln Leu Arg Lys Ser Leu Lys                157
```

Fig. 2

Top Sequence: Temperature Sensitive mutant T4 endonuclease VII nucleic acid sequence (SEQ ID NO:1)

Bottom Sequence: Wild Type T4 endonuclease VII nucleic acid sequence (SEQ ID NO:3)

```
ATGTTATTGA CTGGCAAATT ATACAAAGAA GAAAAACAGA AATTTTATGA TGCACAAAAC   60
ATGTTATTGA CTGGCAAATT ATACAAAGAA GAAAAACAGA AATTTTATGA TGCACAAAAC

GGTAAATGCT TAATTTGCCA ACGAGAACTA AATCCTGATG TTCAAGCTAA TCACCTCGAC  120
GGTAAATGCT TAATTTGCCA ACGAGAACTA AATCCTGATG TTCAAGCTAA TCACCTCGAC

CATGACCATG AATTAAATGG ACCAAAAGCA GGAAAGGTGC GTGGATTGCT TTGTAATCTA  180
CATGACCATG AATTAAATGG ACCAAAAGCA GGAAAGGTGC GTGGATTGCT TTGTAATCTA

TGCAATGCTG CAGAAGGTCA AATGAAGCAT AAATTTAATC GTTCTGGCTT AAAGGGACAA  240
TGCAATGCTG CAGAAGGTCA AATGAAGCAT AAATTTAATC GTTCTGGCTT AAAGGGACAA

GGTGTTGATT ATCTTGAATG GTTAGAAAAT TTACTTACTT ATTTAAAATC CGATTACACC  300
GGTGTTGATT ATCTTGAATG GTTAGAAAAT TTACTTACTT ATTTAAAATC CGATTACACC

CAAAATAATA TTCACCCTAA CTTTGTTGGA GATAAATCAA AGGAATTTTC TCGTTTAGGA  360
CAAAATAATA TTCACCCTAA CTTTGTTGGA GATAAATCAA AGGAATTTTC TCGTTTAGGA

AAAGAGGAAA TGATGGCCGA GATGCTTCAA AGAGGATTTG AATATAATGA ATCTGACACC  420
AAAGAGGAAA TGATGGCCGA GATGCTTCAA AGAGGATTTG AATATAATGA ATCTGACACC
                                                       ▼
AAAACACAAT TAATAGCTTC ATTCAAGAAG CAGCTTAGAA  GAGTTTAAA ATGA         473
AAAACACAAT TAATAGCTTC ATTCAAGAAG CAGCTTAGAA AGAGTTTAAA ATGA         474
```

Fig. 3

Top Sequence: Temperature Sensitive mutant T4 endonuclease VII amino acid sequence (SEQ ID NO:2)

Bottom Sequence: Wild Type T4 endonuclease VII amino acid sequence (SEQ ID NO:4)

```
mlltgklyke ekqkfydaqn gkclicqrel npdvqanhld hdhelngpka gkvrgllcnl
mlltgklyke ekqkfydaqn gkclicqrel npdvqanhld hdhelngpka gkvrgllcnl cnaaegqmkh kfnrsglkgq gvdylewlen lltylksdyt qnnihpnfvg dkskefsrlg
cnaaegqmkh kfnrsglkgq gvdylewlen lltylksdyt qnnihpnfvg dkskefsrlg keemmaemlq rgfeynesdt ktqliasfkk qlrRV
keemmaemlq rgfeynesdt ktqliasfkk qlrKSLK
```

Fig. 4

Wild type Green Fluorescent Protein nucleic acid sequence (SEQ ID NO:5) and amino acid sequence (SEQ ID NO:6)

```
aaa gga gaa gaa ctt ttc act gga gtt gtc cca att ctt gtt gaa tta    48
Lys Gly Glu Glu Leu Phe Thr Gly Val Val Pro Ile Leu Val Glu Leu    16 gat ggc gat gtt aat ggg caa aaa ttc tct gtc agt gga gag ggt gaa    96
Asp Gly Asp Val Asn Gly Gln Lys Phe Ser Val Ser Gly Glu Gly Glu    32 ggt gat gca aca tac gga aaa ctt acc ctt aaa ttt att tgc act act   144
Gly Asp Ala Thr Tyr Gly Lys Leu Thr Leu Lys Phe Ile Cys Thr Thr    48 ggg aag cta cct gtt cca tgg cca aca ctt gtc act act ttc tct tat   192
Gly Lys Leu Pro Val Pro Trp Pro Thr Leu Val Thr Thr Phe Ser Tyr    64 ggt gtt caa tgc ttt tca aga tac cca gat cat atg aaa cgg cat gac   240
Gly Val Gln Cys Phe Ser Arg Tyr Pro Asp His Met Lys Arg His Asp    80 ttt ttc aag agt gcc atg ccc gaa ggt tat gta cag gaa aga act ata   288
Phe Phe Lys Ser Ala Met Pro Glu Gly Tyr Val Gln Glu Arg Thr Ile    96 ttt tac aaa gat gac ggg aac tac aag aca cgt gct gaa gtc aag ttt   336
Phe Tyr Lys Asp Asp Gly Asn Tyr Lys Thr Arg Ala Glu Val Lys Phe   112 gaa ggt gat acc ctt gtt aat aga atc gag tta aaa ggt att gat ttt   384
Glu Gly Asp Thr Leu Val Asn Arg Ile Glu Leu Lys Gly Ile Asp Phe   128 aaa gaa gat gga aac att ctt gga cac aaa atg gaa tac aac tat aac   432
Lys Glu Asp Gly Asn Ile Leu Gly His Lys Met Glu Tyr Asn Tyr Asn   144 tca cat aat gta tac atc atg gca gac aaa cca aag aat gga atc aaa   480
Ser His Asn Val Tyr Ile Met Ala Asp Lys Pro Lys Asn Gly Ile Lys   160 gtt aac ttc aaa att aga cac aac att aaa gat gga agc gtt caa tta   528
Val Asn Phe Lys Ile Arg His Asn Ile Lys Asp Gly Ser Val Gln Leu   176 gca gac cat tat caa caa aat act cca att ggc gat ggc cct gtc ctt   576
Ala Asp His Tyr Gln Gln Asn Thr Pro Ile Gly Asp Gly Pro Val Leu   192 tta cca gac aac cat tac ctg tcc aca caa tct gcc ctt tcc aaa gat   624
Leu Pro Asp Asn His Tyr Leu Ser Thr Gln Ser Ala Leu Ser Lys Asp   208 ccc aac gaa aag aga gat cac atg atc ctt ctt gag ttt gta aca gct   672
Pro Asn Glu Lys Arg Asp His Met Ile Leu Leu Glu Phe Val Thr Ala   224 gct ggg att aca cat ggc atg gat gaa cta tac aaa t                 709
Ala Gly Ile Thr His Gly Met Asp Glu Leu Tyr Lys                   236
```

Fig. 5

Mutant Green Fluorescent Protein nucleic acid sequence (SEQ ID NO:7) and amino acid sequence (SEQ ID NO:8)

```
aaa gga gaa gaa ctt ttc act gga gtt gtc cca att ctt gtt gaa tta    48
Lys Gly Glu Glu Leu Phe Thr Gly Val Val Pro Ile Leu Val Glu Leu    16 gat ggc gat gtt aat ggg caa aaa ttc tct gtc agt gga gag ggt gaa    96
Asp Gly Asp Val Asn Gly Gln Lys Phe Ser Val Ser Gly Glu Gly Glu    32 ggt gat gca aca tac gga aaa ctt acc ctt aaa ttt att tgc act act    144
Gly Asp Ala Thr Tyr Gly Lys Leu Thr Leu Lys Phe Ile Cys Thr Thr    48 ggg aag cta cct gtt cca tgg cca aca ctt gtc act act tag tga        189
Gly Lys Leu Pro Val Pro Trp Pro Thr Leu Val Thr Thr                61 tatggtgttc aatgcttttc aagataccca gatcatatga acggcatga cttttcaag    249 agtgccatgc ccgaaggtta tgtacaggaa agaactatat tttacaaaga tgacgggaac   309
tacaagacac gtgctgaagt caagtttgaa ggtgataccc ttgttaatag aatcgagtta   369
aaaggtattg attttaaaga agatggaaac attcttggac acaaaatgga atacaactat   429
aactcacata atgtatacat catggcagac aaaccaaaga atggaatcaa agttaacttc   489
aaaattagac acaacattaa agatggaagc gttcaattag cagaccatta tcaacaaaat   549
actccaattg gcgatggccc tgtcctttta ccagacaacc attacctgtc cacacaatct   609
gcccttccta aagatcccaa cgaaaagaga gatcacatga tccttcttga gtttgtaaca   669
gctgctggga ttacacatgg catggatgaa ctatacaaat                        709
```

Fig. 6

TEMPERATURE SENSITIVE MUTANT OF BACTERIOPHAGE T4 ENDONUCLEASE VII

RELATED APPLICATION

This application is a continuation of U.S. application Ser. No. 10/246,838, filed Sep. 19, 2002, now abandoned, which is a continuation-in-part of U.S. application Ser. No. 10/180,174, filed Jun. 26, 2002, now abandoned, the entire contents of which are incorporated herein by reference.

BACKGROUND

Maintaining the fidelity of a nucleic acid sequence is of paramount importance in many aspects of molecular biology. During the cloning of a gene sequence, for example, the cloning processes themselves can introduce artifacts into the sequence being cloned, resulting in the isolation of aartificial variant sequence, rather than the true original sequence.

For instance, PCR amplification is known to create mutations at a much higher rate than in vivo propagation (replication) of DNA. The mutation rate will vary with PCR conditions, choice of enzyme, number of replication cycles, etc. After 30 rounds of PCR amplification, it is estimated that between 2% and 10% of the molecules (depending on their size) contain at least one mutation. Thus, when PCR amplified DNA is cloned into a plasmid vector, 2–10% of the cloned inserts will contain mutations. Depending on the downstream application, it is often necessary to sequence the amplified DNA prior to further experimentation. However, since many cloning procedures involve some amplification steps, sequencing can only show if additional variations have been introduced, and cannot demonstrate that the current sequence is true to the original.

In another instance, when assaying sequences within samples for the presence of alterations that indicate the possibility of genetic disease, it becomes critical to know that one is working with the actual sequence originally sampled, rather than an amplification-induced artifact.

In studying variations between the genomes of related organisms and populations, it is also critical to know that one is studying actual sequence differences instead of artifacts. Some assays of genetic diversity within and between human populations, for example, test for the presence of single nucleotide polymorphisms (SNP). Variations in sequences that are actually due to amplification can produce in spurious results.

There is therefore a need in the art for methods that select for PCR amplification products and other nucleic acids that do not contain PCR-induced mutations or other alterations.

SUMMARY OF THE INVENTION

The invention provides for a method of selectively cloning homoduplex nucleic acid molecules, that is, a method of cloning nucleic acid molecules such that the nucleic acid molecules cloned by the method contain a reduced number of heteroduplexes, mismatches, and changes over the parent sequence, relative to nucleic acid molecules not cloned by the method described herein.

For example, in one embodiment, a host strain is provided that contains a temperature sensitive variant of the gene encoding the endonuclease VII from phage T4, e.g., the nucleic acid sequence of SEQ ID NO:1, encoding the amino acid sequence of SEQ ID NO:2. The present invention also provides a method for the selective cloning of amplified nucleic acids with a reduced number of PCR induced mutations, relative to amplified nucleic acids cloned by other methods.

In one embodiment, the invention provides for a host cell for selectively cloning homoduplex DNA molecules. The host cell is competent, and contains a heterologous gene encoding a conditionally expressed and/or conditionally active resolvase, and the host cell can be maintained under conditions where the resolvase is not expressed and/or is repressed and propagated in inactive form. The host cell can be eukaryotic or prokaryotic. The resolvase can be a eukaryotic resolvase, or a bacteriophage resolvase, e.g., bacteriophage T4 endonuclease VII, e.g. a temperature sensitive mutant of bacteriophage T4 endonuclease VII, e.g., the temperature sensitive mutant of bacteriophage T4 endonuclease VII, e.g., SEQ ID NO:2. The resolvase can be an enzyme the expression of which is completely repressed under certain conditions.

The invention also features a method of selectively cloning homoduplex nucleic acid molecules, where the method includes providing one or more host cells containing a heterologous gene encoding a conditionally expressed and/or conditionally active resolvase, transforming the host cells with cloned nucleic acid molecules, and then maintaining the transformed host cells so that the resolvase is expressed and active, and cleaves the cloned heteroduplex molecules, leaving the homoduplex molecules.

The method can further include denaturing and renaturing the nucleic acid molecules before ligation. The method can also include, after action of the resolvase, infecting the cells with helper phage to rescue the homoduplex cloned nucleic acid molecules. The method can also include maintaining the host cells under conditions that prohibit the expression of the resolvase.

In another aspect, the invention features a method of selectively cloning amplified nucleic acid molecules possessing a reduced number of mutations, where the method includes providing one or more host cells containing a heterologous gene encoding a conditionally expressed and/or conditionally active resolvase, transforming the host cells with cloned amplified nucleic acid molecules, and then maintaining the transformed host cells under conditions suitable for expression of resolvase, so that the cloned heteroduplex molecules are cleaved by the resolvase, leaving the homoduplex cloned molecules.

The method can include the further step of denaturing and renaturing the nucleic acid molecules before ligation. The method can include the further step of, after action of the resolvase, infecting the cells with helper phage to rescue the homoduplex ligated nucleic acid molecules. The method can also include the further step of maintaining the host cells under conditions that prohibit the expression of the resolvase. The host cell can be eukaryotic or prokaryotic. The cloning vector can be a phagemid cloning vector or a cosmid vector. The conditionally expressed resolvase can be a eukaryotic resolvase or a bacteriophage resolvase, e.g., bacteriophage T4 Endonuclease VII, e.g., a temperature sensitive mutant of bacteriophage T4 Endonuclease VII, e.g., the temperature sensitive mutant of bacteriophage Endonuclease VII, e.g., the protein of SEQ ID NO:2. The resolvase can be an enzyme the expression of which is completely repressed under certain conditions.

The pool of cloned nucleic acid molecules can contain both hetero- and homoduplex nucleic acids, and the heteroduplex molecules are cleaved by the resolvase in the methods.

In an additional aspect, the invention features a kit comprising a competent host cell containing a heterologous gene encoding a conditionally expressed resolvase, and packaging materials for same. The host cell can be maintained under conditions under which the resolvase is expressed. The kit can also contain a host cell containing an expression vector encoding such a resolvase, for example the temperature sensitive mutant of bacteriophage T4 Endonuclease VII of SEQ ID NO:2, or the host cell can contain an isolated DNA (e.g., SEQ ID NO:1) encoding the temperature sensitive mutant of bacteriophage T4 Endonuclease VII of SEQ ID NO:2.

In any of the above kits, the resolvase can be an enzyme the expression of which is completely repressed under certain conditions. The kits can also contain other reagents, such as PCR reagents, and packaging materials.

The invention also features an isolated protein of a temperature sensitive mutant of bacteriophage T4 Endonuclease VII, where the isolated protein has the amino acid sequence of SEQ ID NO:2, and an isolated nucleic acid encoding such a mutant, where the isolated nucleic acid has the sequence of SEQ ID NO:1.

By the term "heteroduplex" is meant a structure formed between two annealed, nucleic acid strands (e.g., the annealed strands of test and reference nucleic acids, or between template and product in an amplification reaction) in which one or more nucleotides in the first strand are unable to appropriately base pair with those in the second opposing, complementary strand because of one or more mismatches.

Most mismatch-recognizing enzymes and proteins are involved in nucleic acid repair, and so are highly specific. Thus, a duplex possessing just a single mismatch is likely to be recognized by such enzymes and proteins. For heteroduplexes containing high numbers of mismatches, or multiple mismatches clustered closely together, it seems likely that most mismatch recognizing enzymes and proteins would require a spacing of at least three nucleotides between the mismatches in order to resolve each mismatch, in order for the enzyme or protein to be properly situated on the nucleic acid and to act on the mismatch. However, it is not a requirement of the invention that the mismatch recognizing enzyme or protein be able to resolve every mismatch in a heteroduplex nucleic acid. Rather, the enzyme or protein needs only to either (1) bind to the heteroduplex nucleic acid, so that the enzyme/protein-heteroduplex complex can be removed, or (2) cleave in the vicinity of at least one mismatch, so that the resulting products can be selected on the basis of size, e.g., so that products of an expected size are selected, versus smaller (i.e., cleaved) products.

Examples of different types of heteroduplexes include those that exhibit differences over one or several nucleotides, and insertion or deletion mutations, each of which is disclosed in Bhattacharyya and Lilley, *Nucl. Acids. Res.* 17: 6821 (1989). The term "complementary," as used herein, means that two nucleic acids, e.g., DNA or RNA, contain a series of consecutive nucleotides which are capable of forming matched Watson-Crick base pairs to produce a region of double-strandedness (except in the region of mismatch). Thus, adenine in one strand of DNA or RNA pairs with thymine in an opposing complementary DNA strand or with uracil in an opposing complementary RNA strand, and guanine in one strand pairs with cytosine in an opposing strand. The region of pairing is referred to as a "duplex." A duplex may be either a homoduplex or a heteroduplex. In a preferred embodiment, nucleic acid is subjected to amplification, e.g., by PCR, during which it is heat denatured and reannealed to generate homoduplexes and heterodplexes. In general, the methods described herein will work under those conditions that allow the hybridization of complementary strands of nucleic acid. "Mismatch", as used herein, refers to a duplex in which less than all of the nucleotides on one strand are perfectly matched to the other strand (e.g., where nucleotide pairing other than adenosine-thymine or guanine-cytosine occurs, e.g., nucleotide paring such as adenosine-cytosine, adenosine-guanine, adenosine-adenosine, thymine-cytosine, thymine-guanine, thymine-thymine, guanine-guanine, or cytosine-cytosine occurs), where a deletion or insertion of one or more DNA nucleotides on one strand as compared to the other complementary strand occurs (e.g., a deletion of 1, 2, 5, 10, 15, or more nucleotides or an insertion of 1, 2, 5, 10, 15, or more nucleotides occurs), or other mismatches between the two strand of the duplex occurs. DNA mismatches may arise from nucleic acid replication errors, mutagenesis, deamination of 5-methylcytosine, formation of thymidine dimers, nucleic acid recombination, etc.

A "mutation", as used herein, refers to a nucleotide sequence change (i.e., a nucleotide substitution, deletion, or insertion) in an isolated nucleic acid relative to a reference nucleic acid. In one embodiment, the reference nucleic acid is a template-specific nucleic acid used in an amplification reaction.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The terms "transform" and "transfect" as used herein refer to the introduction of foreign DNA into prokaryotic or eukaryotic cells. Transformation of prokaryotic cells may be accomplished by a variety of means known to the art including the treatment of host cells with various salt solutions or nonionic compounds (e.g., $CaCl_2$) to render the cells competent, electroporation treatment, etc. Transfection of eukaryotic cells may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

A "mismatch recognizing" enzyme or protein is an enzyme or protein that recognizes a heteroduplex nucleic acid molecule and binds to it and/or cleaves it. A number of different enzymes qualify as mismatch recognizing enzymes and proteins, including DNA repair enzymes, recombination proteins, and resolvases.

Resolvases are enzymes that process recombinational intermediates. They have the secondary effect of acting on mismatched DNA, which in some respects resembles a recombinational intermediate. "Resolvase", as used herein, refers to an enzyme that cleaves a nucleic acid as the result of the presence of a distortion in a duplex, e.g., a bend, kink or other DNA deviation, e.g., a DNA mismatch, e.g., a single base pair substitution, insertion or deletion, in many different organisms, including bacteria, phage, yeast, and mammals, e.g., humans. The enzyme exerts its effect by mismatch-dependent cleavage, i.e., cleavage of at least one DNA strand, close to the site of DNA distortion, e.g., a DNA mismatch.

Examples of resolvases include, without limitation, T4 endonuclease VII, *Saccharomyces cerevisiae* Endo X1, Endo X2, or Endo X3 (Jensch et al., *EMBO J.* 8:4325, 1989), T7 endonuclease I, *E. coli* MutY (Wu et al., *Proc. Natl. Acad. Sci. USA* 89:8779–8783, 1992), mammalian thymine glycosylase (Wiebauer et al., *Proc. Natl. Acad. Sci. USA* 87:5842–5845, 1990), topoisomerase I from human thymus (Yeh et al., *J. Biol. Chem.* 266:6480–6484, 1991; Yeh et al., *J. Biol. Chem.* 269:15498–15504, 1994), deoxyinosine 3' endonuclease (Yao and Kow, *J. Biol. Chem.* 269:31390–31396, 1994) and Mus81 (Boddy et al., 2001, *Cell* 107:537–48; Chen et al., *Mol. Cell.* 8:1117–27, 2001). In one embodiment, the resolvase is isolated from a bacteriophage, e.g., bacteriophage T3, T4 or T7. In another embodiment, the resolvase is a mutated form (nucleic acid sequence, SEQ ID NO:1; amino acid sequence SEQ ID NO:2; FIG. 1) of the wild type endonuclease VII of phage T4 (GenBank Accession No.: X12629; nucleic acid sequence, SEQ ID NO:3; amino acid sequence SEQ ID NO:4; FIG. 2).

"Mismatch-dependent cleavage", as used herein, refers to a characteristic of an enzyme such as a resolvase. An enzyme has a mismatch-dependent cleavage activity if it cleaves at a mismatch, at a significantly higher rate, than it would cleave a corresponding perfectly matched sequence. In preferred embodiments, an enzyme with a mismatch-dependent cleavage is at least about 5%, 15%, 25%, 50%, 75% or 100% more efficient at cleaving at a mismatch than at a corresponding perfectly matched sequence.

As used herein, "conditionally expressed" and "conditionally active" refer to the expression of a mismatch recognizing enzyme or protein, which is only present and functional under certain conditions.

In one embodiment, the enzyme or protein is "conditionally expressed", that is, the protein is only active under certain conditions, i.e., permissive conditions. Under nonpermissive conditions, the enzyme or protein is not produced, and is not present.

In another embodiment, the enzyme or protein is "conditionally active", that is, the gene encoding the enzyme or protein is always present, but is only active under certain conditions. In one such embodiment, the enzyme has a temperature sensitive mutation that renders the protein non-functional (i.e., inactive) at (e.g. warm temperatures, e.g. 37–42° C.), and functional (i.e., active) at colder temperatures. In one such embodiment, the gene encoding the mutant protein or enzyme has a nonsense mutation that results in the translation of a truncated protein. In a preferred embodiment, "conditionally-expressed" or "conditionally active" refer to the expression of a temperature sensitive mutant T4 endonuclease VII protein that is active and functional but also lethal to the host cells at 25° C., for example, the temperature sensitive mutant T4 endonuclease VII protein, SEQ ID NO:2, encoded by SEQ ID NO:1.

A "host cell" is a cell which has been transformed or transfected, or is capable of transformation or transfection by a heterologous polynucleotide sequence. Host cells can be prokaryotic or eukaryotic, mammalian, plant, or insect, and can exist as single cells, or as a collection, e.g., as a culture, or in a tissue culture, or in a tissue or an organism. In a preferred embodiment, prokaryotic host cells are bacteria that harbor the F' episome that enables f1 phage rescue as described herein. Host cells can also be derived from normal or diseased tissue from a multicellular organism, e.g., a mammal. Host cell, as used herein, is intended to include not only the original cell which was transformed with a nucleic acid, but also descendants of such a cell, which still contain the nucleic acid.

In one embodiment, the "host cell" is a cell which contains a mismatch recognizing enzyme or protein, where the activity of the enzyme or protein can be controlled, i.e., be regulated by the one practicing the invention. The mismatch recognizing enzyme or protein can be native to the cell, or can be heterologous, that is, introduced into the cell, e.g., transfected or transformed into the cell. The enzyme or protein can also be one which was originally native to the host cell, but has been altered so that it is now capable of being controlled.

"Heterologous" nucleic acid refers to nucleic acid not naturally located in the cell, or in a chromosomal site of the cell. Preferably, the heterologous nucleic acid includes a nucleic acid foreign to the cell.

As used herein, "a mixture of DNA molecules" or "mixture of nucleic acid molecules", refer to DNA or other nucleic acid molecules which, when aligned, may vary in sequence at one or more positions or at no positions. In a preferred embodiment, the terms refer to DNA or other nucleic acid that was amplified, e.g., by the polymerase chain reaction.

As used herein, the term "amplified", when applied to a nucleic acid sequence, refers to a process whereby one or more copies of a particular nucleic acid sequence is generated from a template nucleic acid, preferably by the method of polymerase chain reaction (Mullis and Faloona, 1987, *Methods Enzymol.* 155:335). "Polymerase chain reaction" or "PCR" refers to an in vitro method for amplifying a specific nucleic acid template sequence. The PCR reaction involves a repetitive series of temperature cycles and is typically performed in a volume of 50–100 µl. The reaction mix comprises dNTPs (each of the four deoxynucleotides dATP, dCTP, dGTP, and dTTP), primers, buffers, thermostable DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers" or "a set of PCR primers" can comprise two, three, four or more primers. Other methods of amplification include, but are not limited to, ligase chain reaction (LCR), polynucleotide-specific based amplification (NSBA), or any other method known in the art.

As used herein, "nucleic acid polymerase" refers to an enzyme that catalyzes the polymerization of nucleotides. Generally, the enzyme will initiate synthesis at the 3'-end of the primer annealed to a nucleic acid template sequence, and will proceed in the 5'-direction along the template. "DNA polymerase" catalyzes the polymerization of deoxynucleotides. Known DNA polymerases include, for example, *Pyrococcus furiosus* (Pfu) DNA polymerase, *E. coli* DNA polymerase I, T7 DNA polymerase, *Thermus thermophilus*

(Tth) DNA polymerase, *Bacillus stearothermophilus* DNA polymerase, *Thermococcus litoralis* (Tli) DNA polymerase (also referred to as Vent DNA polymerase), *Thermotoga maritima* (UlTma) DNA polymerase, *Thermus aquaticus* (Taq) DNA polymerase, and *Pyrococcus GB-D* (PGB-D) DNA polymerase. The polymerase activity of any of the above enzyme can be defined by means well known in the art. One unit of DNA polymerase activity, according to the subject invention, is defined as the amount of enzyme which catalyzes the incorporation of 10 nmoles of total dNTPs into polymeric form in 30 minutes at 72° C.

As used herein, "thermostable" refers to an enzyme (or protein) which is stable and active at temperatures as great as preferably between about 90–100° C. and more preferably between about 70–98° C. as compared to a non-thermostable form of an enzyme with a similar activity that are typically denatured at such elevated temperatures. For example, a representative thermostable nucleic acid polymerase isolated from *Thermus aquaticus* (Taq) is described in U.S. Pat. No. 4,889,818 and a method for using it in conventional PCR is described in Saiki et al. (1988, *Science* 239:487). Another representative thermostable nucleic acid polymerase isolated from *P. furiosus* (Pfu) is described in Lundberg et al. (1991, *Gene* 108:1–6). Additional representative temperature stable polymerases include, e.g., polymerases extracted from the thermophilic bacteria *Thermus flavus*, *Thermus ruber*, *Thermus thermophilus*, *Bacillus stearothermophilus* (which has a somewhat lower temperature optimum than the others listed), *Thermus lacteus*, *Thermus rubens*, *Thermotoga maritima*, or from thermophilic archaea *Thermococcus litoralis*, and *Methanothermus fervidus*.

As used herein, a "PCR ligation mix" or "amplification ligation mix" refers to the reaction mix after ligation has occurred in which an amplified nucleic acid fragment is ligated to a recombinant nucleic acid vector that is capable of autonomous replication within a host cell. In a preferred embodiment, the recombinant nucleic acid vector is a phagemid or a cosmid vector.

As used herein, "competent" cells refers to host cells that are primed for the uptake of nucleic acids. Competent cells are treated to make their cell membranes more permeable in order to facilitate the entry of heterologous nucleic acids.

The term "recombinant DNA vector" or "recombinant nucleic acid vector" as used herein refers to DNA or other nucleic acid sequences containing a desired coding sequence and appropriate sequences necessary for the expression of the operably linked coding sequence in a particular host organism. Sequences necessary for expression in prokaryotes include a promoter, optionally an operator sequence, a ribosome-binding site and possibly other sequences. Eukaryotic cells are known to utilize promoters, polyadenylation signals and enhancers.

As used herein, "helper phage" refers to a normal wild-type version of the phage, which typically grows along with a specialized phage such as a phagemid (Bluescript, pUC and the like) and supplies whatever functions are necessary for generating phage particles. In one embodiment, the "helper phage" is M13KO7, a M13 phage that is able to replicate in *E. coli* in the absence of phagemid DNA. In the presence of a phagemid bearing a wild-type M13 or f1 origin, single-stranded phagemid is packaged preferentially and secreted into the culture medium.

As used herein, "rescue" refers to the recovery of homoduplex nucleic acid molecules that were not degraded according to the invention, by one or more mismatch recognizing enzymes or proteins.

As used herein, "reducing the amount of nucleic acid heteroduplexes" or "reducing the number of nucleic acid heteroduplexes" refers to a decrease in the number of nucleic acid heteroduplexes in a mixture of nucleic acid molecules as a result of the method of the invention. In one embodiment, the amount and/or number of nucleic acid heteroduplexes are reduced by enzymatic cleavage by T4 endonuclease VII in a host cell. In a preferred embodiment, the decrease in the amount or number of nucleic acid heteroduplexes in a mixture of nucleic acid molecules treated according to the invention is at least 75%, preferably 90%, more preferably 99% and most preferably 100% (i.e., no heteroduplexes remain) as compared to the amount or number of nucleic acid heteroduplexes in a mixture of nucleic acid molecules not treated according to the invention, e.g., not enzymatically cleaved by T4 endonuclease VII in a host cell.

As used herein, "maintaining" the host cells refers to those experimental conditions of IPTG induction, competence to nucleic acid transformation and non-permissive or non-active conditions, i.e., conditions where the mismatch recognizing enzyme or protein is not active. In one embodiment, maintenance of the cells is at warm temperatures, e.g., 37–42° C., i.e., high temperature that allows cell viability, expression of non-functional T4 endonuclease VII, digestion of heteroduplex ligated DNA and rescue of homoduplex DNA with f1 helper phage before the onset of host cell death.

BRIEF DESCRIPTION OF THE DRAWINGS

FIG. 1 is a diagram showing the nucleic acid (SEQ ID NO:1) and amino acid (SEQ ID NO:2) sequences of the temperature-sensitive mutant T4 endonuclease VII.

FIG. 2 is a diagram showing the nucleic acid (SEQ ID NO:3) and amino acid (SEQ ID NO:4) sequences of the wild-type T4 endonuclease VII.

FIG. 3 is a diagram showing the alignment of the nucleic acid sequences of the temperature-sensitive mutant T4 endonuclease VII nucleic acid sequence (SEQ ID NO:1) and the wild type T4 endonuclease VII nucleic acid sequence (SEQ ID NO:3), showing that the mutant has a single base deletion at position 461 of the wild type sequence.

FIG. 4 is a diagram showing the alignment of the amino acid sequences of the temperature-sensitive mutant T4 endonuclease VII nucleic acid sequence (SEQ ID NO:2) and the wild type T4 endonuclease VII amino acid sequence (SEQ ID NO:4), showing that the mutant protein is missing the last two amino acids of the wild type protein, and that the last two amino acids of the mutant protein are substituted relative to the corresponding two amino acids in the wild-type protein.

FIG. 5 is a diagram showing the nucleic acid (SEQ ID NO:5) and amino acid (SEQ ID NO:6) sequences of a wild-type Green Fluorescent Protein.

FIG. 6 is a diagram showing the nucleic acid (SEQ ID NO:7) and amino acid (SEQ ID NO:8) sequences of a mutant Green Fluorescent Protein comprising a premature stop codon.

DETAILED DESCRIPTION

The invention provides for a method of selecting homoduplex nucleic acid molecules out of a mixture of homoduplex and heteroduplex nucleic acid molecules, that is, of selecting out those nucleic acid molecules that contain a reduced number of heteroduplexes, mismatches, and changes relative to the parent sequence, compared to nucleic acid molecules not selected by the methods described herein. The method can be done in vivo, that is, within a host cell, by cloning the nucleic acid molecules to be selected into the host cell, where a mismatch recognizing enzyme or protein acts on the heteroduplex molecules, e.g., by cleaving them at or near the site of the mismatch.

In one embodiment, the subject invention provides for a host strain that contains a temperature sensitive variant of the gene encoding the endonuclease VII from phage T4. Using this host strain, the invention features a novel cloning method that selects for nucleic acids. e.g., PCR products, that do not contain mutations, e.g., PCR generated mutations.

In one embodiment, the invention provides for a competent host cell which specifically cleave a mismatched nucleic acid it contains. Such a cell contains a plasmid containing a heterologous, conditionally-active resolvase, e.g., a T4 endonuclease VII enzyme which has been mutated to be conditionally active. In one embodiment, the enzyme has been mutated and is temperature-sensitive, e.g., is active when the cells are grown at normal temperatures, and inactive when the cells are grown at non-permissive (e.g., elevated) temperatures. Alternatively, a true conditionally-expressed resolvase can be used, that is, a resolvase the expression of which is completely repressed under certain conditions.

The normal T4 endonuclease VII enzyme cannot be expressed and stably maintained in *E. coli* because it is lethal to those cells into which it is produced. This enzyme is a resolvase, and cleaves double stranded DNA a few bases downstream of any perturbation in the DNA. It therefore cleaves nucleic acids in which the two complementary strands are not perfectly matched. *E. coli* possesses its own DNA repair enzymes, but T4 endonuclease VII, when cloned into *E. coli*, produces a double strand blunt cleavage at mismatches, and such cleavages cannot be repaired. Such mismatches arise due to replication errors. Therefore, when normal (i.e., unmutated) T4 endonuclease VII is cloned into *E. coli* and expressed, it cleaves the host cell's DNA immediately after it has been synthesized.

In vitro, T4 endonuclease VII cleaves mismatched DNA, but will also digest homoduplex DNA at a reduced level. In vivo, the enzyme's specificity is much higher.

In one embodiment described herein, a mutated T4 endonuclease VII gene has been introduced into *E. coli* cells. This mutated enzyme gene encodes an altered endonuclease enzyme that contains a temperature-sensitive mutation, so that the enzyme is active at permissive (e.g., 25° C.) temperatures, but exhibits little or no activity when the host cells are grown at higher temperatures (e.g., 37° C.–42° C.). In the mutated enzyme shown in FIG. 1 (SEQ ID NO:2), the enzyme is actually expressed when the host cells are grown or maintained at higher temperatures, but the protein folds incorrectly, resulting in little or no activity at those temperatures.

Once the gene encoding the mutated endogenous endonuclease has been transformed into one or more host cells, the cells are grown at the non-permissive temperature, and rendered competent via any methods known in the art. The cells are then briefly maintained at the permissive temperature for 0–3 hours to allow the cell(s) to produce active resolvase. The cells are then frozen and stored, or are used immediately.

Double-stranded nucleic acids (e.g., amplification products) from which one wishes to select perfectly matched products (e.g., homoduplexes) are then ligated into an appropriate plasmid. The host cells are then thawed (if necessary), and are transformed with the plasmids containing the double-stranded nucleic acid. The active resolvase the acts to degrade any nucleic acid containing a perturbation, e.g., a mismatch.

One can rescue those plasmids containing homoduplexes by use of an F1 helper phage. Such a phage excises plasmids, packages the DNA into a phage particle, and infects the phage-plasmid hybrid molecules (called phagemids) into another F strain of bacteria. Preferably, cells of this other F strain of bacteria are also in the mixture of competent cells, so that the transfer (i.e., the rescue) of the plasmids can be done immediately.

In vitro amplification of nucleic acids (e.g., by polymerase chain reaction) tends to be highly error-prone. If a mutation occurs in a very early cycle, it is possible that the final amplification products will include a high proportion of perfectly matched products, which are yet mutated relative to the original template nucleic acid. The possibility of such an occurrence can be reduced by denaturing and reannealing the final PCR products, to increase the number of mismatches available for action by the resolvase. The number of cloned products will perforce be reduced, but this method increases the chances of removing "false" homoduplexes.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); (Harlow, E. and Lane, D.) *Using Antibodies: A Laboratory Manual* (1999) Cold Spring Harbor Laboratory Press; and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference in their entirety.

The invention provides a method for the cloning of a PCR product that has a reduced number of PCR-induced mutations, relative to products cloned by other methods. The invention therefore provides for primers specific for a test DNA template, methods of primer synthesis, methods of DNA amplification and cloning into a phagemid cloning vector. The invention also features host cells that harbor an expression vector containing a temperature sensitive mutant of T4 endonuclease VII. The method therefore provides for methods of mutagenesis and screening procedures required for the identification and isolation of host cells containing a temperature sensitive mutant of T4 endonuclease VII. The invention also provides protocols for the generation of competent host cells, a denaturation and renaturation of the ligated DNA, transformation of the competent host cells with the mixture of DNA homoduplex and heteroduplex molecules, maintenance of the host cells at a temperature permitting the expression of functional T4 endonuclease VII and subsequent rescue by f1 helper phage.

Primers According to the Invention

The invention provides for oligonucleotide primers useful for amplifying DNA or RNA sequences.

Primer Design

Primers may be selected manually by analyzing the template sequence. Computer programs, however, are also available in selecting primers to generate an amplified product with a designed length, e.g., primer premier 5 (available at the website of the company Premierbiosoft) and primer3 (available at the website of the Whitehead Institute for Biomedical Research, Cambridge, Mass., U.S.A).

It is known in the art that primers that are about 20–25 bases long and with 50% G-C content will work well at annealing temperature at about 52–58° C. These properties are preferred when designing primers for the subject invention. Longer primers, or primers with higher G-C contents, have annealing optimums at higher temperatures; similarly, shorter primers, or primers with lower G-C contents, have optimal annealing properties at lower temperatures. A convenient, simplified formula for obtaining a rough estimate of the melting temperature of a primer 17–25 bases long is as follows:

Melting temperature (Tm in ° C.)=4×(#of G+#of C)+2×(#of A+#of T)

Shorter fragments are amplified more efficiently than longer fragments although target of more than 10 kb can be successfully amplified. Preferably the primers are chosen so as to amplify an entire coding region.

In accordance with the preferred embodiments, optimal results have been obtained using primers, which are 19–25 in length. However, one skilled in the art will recognize that the length of the primers used may vary. For example, it is envisioned that shorter primers containing at least 15, and preferably at least 17, may be suitable. The exact upper limit of the length of the primers is not critical. However, typically the primers will be less than or equal to approximately 50 bases, preferably less than or equal to 30 bases.

Primer Synthesis Methods for synthesizing primers are available in the art. The oligonucleotide primers of this invention may be prepared using any conventional DNA synthesis method, such as, phosphotriester methods such as described by Narang et al. (1979, *Meth. Enzymol.* 68:90) or Itakura (U.S. Pat. No. 4,356,270), or and phosphodiester methods such as described by Brown et al. (1979, *Meth. Enzymol.* 68:109), or automated embodiments thereof, as described by Mullis et al. (U.S. Pat. No. 4,683,202). Also see particularly Sambrook et al. (1989), Molecular Cloning: A Laboratory Manual (2d ed.; Cold Spring Harbor Laboratory: Plainview, N.Y.), herein incorporated by reference in its entirety.

Useful DNA Polymerases and Reverse Transcriptases

DNA polymerases and their properties are described in detail in, among other places, *DNA Replication 2nd edition*, Kornberg and Baker, W. H. Freeman, New York, N.Y. (1991).

Known conventional DNA polymerases include, for example, *Pyrococcus furiosus* (Pfu) DNA polymerase (Lundberg et al., 1991, *Gene,* 108:1, provided by Stratagene, La Jolla, Calif., USA), *Pyrococcus woesei* (Pwo) DNA polymerase (Hinnisdaels et al., 1996, *Biotechniques,* 20:186–8, provided by Boehringer Mannheim, Roche Molecular Biochemicals, Indianapolis, Ind., USA), *Thermus thermophilus* (Tth) DNA polymerase (Myers and Gelfand 1991, *Biochemistry* 30:7661), *Bacillus stearothermophilus* DNA polymerase (Stenesh and McGowan, 1977, *Biochim Biophys Acta* 475:32), *Thermococcus litoralis* (Tli) DNA polymerase (also referred to as Vent DNA polymerase, Cariello et al., 1991, *Polynucleotides Res,* 19: 4193, provided by New England Biolabs, Beverly, Mass., USA), 9° Nm DNA polymerase (discontinued product from New England Biolabs, Beverly, Mass., USA), *Thermotoga maritima* (Tma) DNA polymerase (Diaz and Sabino, 1998 *Braz J. Med. Res,* 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, *Appl. Environ. Microbiol.* 63:4504), JDF-3 DNA polymerase (from *Thermococcus* sp. JDF-3, Published International patent application WO 0132887), *Pyrococcus GB-D* (PGB-D) DNA polymerase (also referred as Deep-Vent DNA polymerase, Juncosa-Ginesta et al., 1994, *Biotechniques,* 16:820, provided by New England Biolabs, Beverly, Mass., USA), UlTma DNA polymerase (from thermophile *Thermotoga maritima*; Diaz and Sabino, 1998 *Braz. J. Med. Res.* 31:1239; provided by PE Applied Biosystems, Foster City, Calif., USA), Tgo DNA polymerase (from *Thermococcus gorgonarius,* provided by Roche Molecular Biochemicals, Indianapolis, Ind., USA), *E. coli* DNA polymerase I (Lecomte and Doubleday, 1983, *Polynucleotides Res.* 11:7505), T7 DNA polymerase (Nordstrom et al., 1981, *J. Biol. Chem.* 256:3112), and archaeal DP1/DP2 DNA polymerase II (Cann et al., 1998, *Proc Natl Acad Sci USA* 95:14250–5). The polymerization activity of any of the above enzymes can be defined by means well known in the art. One unit of DNA polymerization activity of conventional DNA polymerase, according to the subject invention, is defined as the amount of enzyme which catalyzes the incorporation of 10 nmoles of total deoxynucleotides (dNTPs) into polymeric form in 30 minutes at optimal temperature (e.g., 72° C. for Pfu DNA polymerase). Assays for DNA polymerase activity and 3'–5' exonuclease activity can be found in *DNA Replication 2nd Ed.*, Kornberg and Baker, supra; *Enzymes*, Dixon and Webb, Academic Press, San Diego, Calif. (1979), as well as other publications available to the person of ordinary skill in the art.

When using the subject compositions in reaction mixtures that are exposed to elevated temperatures, e.g., during the PCR technique, use of thermostable DNA polymerases is preferred.

Reverse transcriptases useful according to the invention include, but are not limited to, reverse transcriptases from HIV, HTLV-1, HTLV-II, FeLV, FIV, SIV, AMV, MMTV, MoMuLV and other retroviruses (for reviews, see for example, Levin, 1997, *Cell* 88:5–8; Verma, 1977, *Biochim. Biophys. Acta* 473:1–38; Wu et al., 1975, *CRC Crit. Rev. Biochem.* 3:289–347).

Phagemid Cloning Vectors Useful According to the Invention.

Methods well known to those skilled in the art can be used to construct phagemid cloning vectors containing a polynucleotide of the invention. These methods include in vitro recombinant DNA techniques, synthetic techniques and in vivo recombination/genetic recombination. See, for example, the techniques described in Sambrook & Russell, *Molecular Cloning: A Laboratory Manual,* $3^{rd}$ Edition, Cold Spring Harbor Laboratory, N.Y. (2001) and Ausubel et al., *Current Protocols in Molecular Biology* (Greene Publishing Associates and Wiley Interscience, N.Y. (1989).

In a preferred embodiment, the invention provides for phagemid cloning vectors that typically contain an origin of DNA replication, e.g., a colE1 origin or any of a number of plasmid origins of replication, and also a F1 origin of replication that enables phage controlled DNA replication. A number of phagemid vectors are commercially available such as the pBluescript II phagemids (Stratagene Catalog #212205, #212206, #212207 and #212208) which has an extensive polylinker with 21 unique restriction enzyme recognition sites. Flanking the polylinker are T7 and T3

RNA polymerase promoters that can be used to synthesize RNA in vitro. pBluescript II phagemids contain a 454-bp filamentous f1 phage intergenic region (M13 related), which includes the 307-bp origin of replication. The (+) and (−) orientations of the f1 intergenic region allow the rescue of sense or antisense ssDNA by a helper phage which promotes the packaging of the replicated single stranded phagemid DNA into infectious phage particles that are secreted into the media. Phagemids therefore permit the rescue of cloned sequences without the need for traditional subcloning methods.

Expression Vectors According to the Invention

The invention provides for vectors for the expression of variants of endonuclease VII of phage T4. Appropriate cloning and expression vectors for use with prokaryotic and eukaryotic hosts are described by Sambrook et al., in *Molecular Cloning: A Laboratory Manual*, Second Edition, Cold Spring Harbor, N.Y. (1989), the disclosure of which is incorporated herein by reference in its entirety.

The DNA sequence in the expression vector is operatively linked to an appropriate expression control sequence(s) (promoter) to direct mRNA synthesis. Examples of such promoters include but are not limited to: LTR or SV40 promoter in mammalian cells, the *E. coli*. lac or trp, the phage $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*. The vector containing the appropriate DNA sequence as hereinabove described, as well as an appropriate promoter or control sequence, may be employed to transform an appropriate host to permit the host to express the protein.

In one embodiment, the variant T4 endonuclease VII genes are cloned into a pACYC 184 expression vector that contains a multiple cloning site (MCS), the lac operator, and P15A that is compatible plasmids containing a colE1 origin of replication (Nakano et al. (1995) *Gene* 162: 157–158). In another embodiment, the mismatch recognizing enzyme or protein is cloned into a cosmid vector.

Host Cells Useful According to the Invention

The present invention further provides host cells containing the vectors of the present invention, wherein the nucleic acid has been introduced into the host cell using known transformation, transfection or infection methods. The host cell can be a eukaryotic host cell, such as a mammalian cell, a plant cell, a lower eukaryotic host cell, such as a yeast cell, or the host cell can be a prokaryotic cell, such as a bacterial cell.

Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

In yeast, a number of vectors containing constitutive or inducible promoters may be used. For a review see, *Current Protocols in Molecular Biology*, Vol. 2, Ed. Ausubel et al., Greene Publish. Assoc. & Wiley Interscience, Ch. 13 (1988); Grant et al. (1987) "Expression and Secretion Vectors for Yeast", *Methods Enzymol.* 153:516–544; Glover, *DNA Cloning*, Vol. II, IRL Press, Wash., D.C., Ch. 3 (1986); Bitter, *Heterologous Gene Expression in Yeast, Methods Enzymol.* 152:673–684 (1987); and *The Molecular Biology of the Yeast Saccharomyces*, Eds. Strathem et al., Cold Spring Harbor Press, Vols. I and II (1982).

In a preferred embodiment, the host of the invention is a prokaryotic cell such as *E. coli*, other enterobacteriaceae such as *Salmonella typhimurium*, bacilli, various pseudomonads, or other prokaryotes which can be transformed, transfected, and/or infected. The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell, which drives expression of the polynucleotides in the cell.

In another preferred embodiment, the host strain XL1-Blue MRF Stratagene (Catalog #200301); Genotype: k(mcrA)183 k(mcrCB-hsdSMR-mrr)173 endA1 supE44 thi-1 recA1 gyrA96 relA1 lac [F proAB lacI<ZkM15 Tn10 (Tet')] is used for the propagation of pBluescript II phagemids and for transformation of recombinant phagemids.

In another preferred embodiment, the host cell conditionally expresses one or more resolvases of prokaryotic or eukaryotic origin.

In another preferred embodiment, the host cell of the invention is XL1-Blue MRF that conditionally expressed a variant of the endonuclease VII of T4 phage.

In another preferred embodiment, the host cell of the invention is XL1-Blue MRF that conditionally expressed a temperature-sensitive mutant of the endonuclease VII of T4 phage.

Generation Of Conditionally Expressed Endonuclease VII of Phage T4

The T4 endonuclease VII gene product, if expressed in *E. coli*, is lethal to the host cells since during the normal bacterial life cycle, replication errors become sites for endonuclease cleavage and ultimately leads to the destruction of the chromosomal integrity and cell death. To overcome the inherent toxicity, the T4 endonuclease VII gene is randomly mutagenized, cloned into an expression vector and then transformed into an appropriate host cell such as XL1-Blue MRF. Transformants are then screened for the presence of conditional lethal mutations within the T4 endonuclease VII open reading frame that permit cell growth at permissive conditions but not a non-permissive conditions.

Mutagenesis

Methods of random mutagenesis that generate one or more randomly-situated mutations are known in the art. One example of such a method is to clone the sequence of interest into a strain of *E. coli* that has a high spontaneous mutation rate (i.e., a "mutator strain", e.g., *E. coli* strain XL1-RED). It was this method that was used to generate the mutant T4 endonuclease VII of the present invention.

An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase. The resulting PCR product is cloned into multiple cloning site downstream of the IPTG inducible lactose promoter of the expression vector, pACYC 184 using standard recombinant DNA techniques that are known to one of skill in the art. The recombinant expression vector is then transformed into competent XL1-Blue MR and plated out on Luria broth plates containing chloramphenicol (50 μg/ml) according to standard procedure.

Screening for Temperature Sensitive Mutants of T4 Endonuclease VII

Chloramphenicol resistant colonies are then screened in the presence of the IPTG inducer (0.1–1 mM) for mutants of T4 endonuclease VII that are temperature sensitive. These mutants grow normally at temperatures of 37° C. and above, where the enzyme is inactive, but are incapable of growth at room temperature whether the T4 endonuclease expression was induced or not. The nucleotide sequence of the temperature sensitive mutant of T4 endonuclease VII is provided in SEQ ID NO:1. The wild type version is shown in SEQ ID NO:2. Host cells carrying the temperature sensitive T4 endonuclease VII gene can then be propagated at the permissive temperature of 37° C.

Generation of Competent Cells

Prior to making these cells competent for transformation (chemical or electrocompetent) expression of the temperature sensitive T4 endonuclease VII enzyme is turned on by addition of IPTG inducer (1 mM) and the inactive enzyme reactivated by its presumed correct folding at temperatures below 37° C. (see Example 2, below).

Methods of generating competent cells are well known to those skilled in the art. Typical methods of generating competent cells comprise growing cells to log phase or early stationary phase and exposing the cells to $CaCl_2$ or other cationic compound (see, e.g., Sambrook et al., In *Molecular Cloning: a Laboratory Manual,* 2nd Edition, eds. Sambrook et al., Cold Spring Harbor Laboratory Press, (1989)). Cells can be contacted immediately with heterologous DNA or frozen in glycerol or DMSO for subsequent use. Upon thawing to 4° C. and contacting with plasmid DNA, frozen competent cells typically have transformation efficiencies of $1\times10^{5-1\times10^9}$ transformants/μg of plasmid DNA.

Generation of Electrocompetent Cells

Electroporation has also been used to transform cells (see, e.g., Dower et al., *Nucleic Acids Research* 16:6127–6145 (1988); Taketo, *Biochimica et Biophysica Acta* 949:318–324 (1988); Chassy and Flickinger, *FEMS Microbiology Letters* 44:173–177 (1987); and Harlander, *Streptococcal Genetics,* eds. Ferretti and Curtiss, American Society of Microbiology, Washington, D.C., pp. 229–233 (1987)). Electroporation methods rely on creating temporary holes in cell membranes by exposing cells to a high voltage electric impulse to facilitate the uptake of heterologous nucleic acids (see, e.g., Andreason and Evans, *Biotechniques* 6:650–660 (1988)). Cells exposed to an electroporation buffer (e.g., 10–15% glycerol) are generally stored by freezing to provide a supply of electrocompetent cells (see, e.g., U.S. Pat. No. 6,004,804).

DNA Denaturation and Renaturation According to the Invention

The formation of a duplex is accomplished by denaturing and then annealing two homologous and complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially, or completely, complementary.

Preferably, single-stranded DNA is prepared by denaturing double-stranded test DNA in distilled water with heat (i.e., between 90° C. and 100° C.). Those skilled in the art will appreciate that DNA denaturation can also be accomplished by heat denaturation, followed by renaturation at progressively lower temperatures. Heteroduplex formation between the different strands of a heat denatured test DNA is performed in 50 μl (total volume) containing 1 times annealing buffer as previously described (Cotton, *Methods in Molecular Biology* 9:39 (1991)) except that the annealing temperature is set at 65° C. for 1 hour followed by 20 minutes at room temperature.

Phage Rescue According to the Invention

M13KO7 (Stratagene (La Jolla, Calif., USA) Catalog No.:#N0315S) is an M13 derived helper phage that carries the mutation Met40Ile in gII, the origin of replication from P15A and the kanamycin resistance gene from Tn903 both inserted within the M13 origin of replication. M13KO7 is able to replicate in the absence of phagemid DNA. In the presence of a phagemid bearing a wild-type M13 or f1 origin such as pBluescript II, single-stranded phagemid is packaged preferentially and secreted into the culture medium. Since these filamentous helper phages (M13, f1) will not infect *E. coli* without an F episome coding for pili, it is essential to use XL1-Elue MRF or a similar strain containing the F episome. Typically, 30–50 pBluescript II molecules are packaged/helper phage DNA molecule. pBluescript II phagemids are offered with the IG region in either of two orientations: pBluescript II (+) is replicated such that the sense strand of the β-galactosidase gene is secreted within the phage particles; pBluescript II (−) is replicated such that the antisense strand of the β-galactosidase gene is secreted in the phage particles. Yields of single-stranded (ss)DNA depend on the specific insert sequence. For most inserts, over 1 pg of ssDNA can be obtained from a 1.5-ml mini-culture.

Generation of Competent Cells Harboring a Temperature Sensitive T4 Endonuclease VII In vitro experiments demonstrate that T4 endonuclease VII not only digests heteroduplex DNA at the sites of mismatch but also homoduplex DNA at random (but reproducible) sites. These preliminary experiments thus established that, unless other discriminatory factors are discovered, T4 endonuclease VII can only be used in an in vivo setting, where the accuracy of the enzyme ensures that homoduplex DNA is never cleaved. However, the T4 endonuclease gene product, if expressed in *E. coli*, is lethal to the host cells since during the normal bacterial life cycle, replication errors (which are normally repaired post-replicationally) become sites for endonuclease cleavage and leads to the destruction of the chromosomal integrity and eventual cell death. To overcome this problem, T4 endonuclease VII was mutagenized (see above), cloned into an pACYC expression vector downstream of the lactose promoter and transformed into a XL1-Blue MRF containing a pCALnEK plasmid that expresses the lactose high affinity repressor (lacI$^q$) and a second expression plasmid (R6K) that enhances the repression in this setting. Transformants were then screened for the presence of temperature sensitive mutations and a conditional lethal mutant was isolated that grows normally at temperatures above 37° C. (enzyme inactive) but were incapable of growth at room temperature whether the T4 endonuclease expression was induced or not.

Chemical methods of making competent cells as well as electrocompetent cells are well known in the art cells (see U.S. Pat. Nos. 5,512,468; 6,338,965 and 6,040,184 and references cited therein). Prior to DNA transformation, expression of the temperature sensitive T4 endonuclease VII can be both turned on and the inactive enzyme reactivated by its presumed correct folding at temperatures below 37° C. During this relatively brief period, the *E. coli* host cells have not yet died (and thus can be transformed with plasmid DNA) but will contain active endonuclease to cleave incoming DNA containing a mismatch.

PCR Amplification and Ligation

Methods for PCR cloning of a target DNA sequence are well known to those skilled in the art. A number of kits are now commercially available that provide all reagents and reaction conditions for the generation of PCR DNA fragments and subsequent cloning into a phagemid cloning vector. In one embodiment of the present invention, PCR fragments are generated using a TOPO cloning kit (InVitrogen, San Diego, Calif., USA), PCR-Script® cloning kit (Stratagene, La Jolla, Calif., USA); catalog # 211188), or other method or kit. PCR products are incubated with one of the predigested PCR-Script phagemid cloning vectors, SrfI and T4 DNA ligase. Using the restriction enzyme in the ligation reaction maintains a high-steady-state concentration of digested vector DNA and allows the use of nonphosphorylated, unmodified PCR primers. The ligation efficiency of blunt-ended DNA fragments is increased by the simultaneous, opposite reactions of the SrfI restriction enzyme and T4 DNA ligase on nonrecombinant vector DNA. The PCR-Script cloning kits allow rapid and efficient cloning of all PCR products, regardless of the PCR enzyme used to generate the inserts. PCR-Script kits also include the StrataPrep® PCR purification kit for easy and efficient removal of primers and nonspecific amplification products smaller than 100 bp.

The PCR product is diluted with distilled water and heat denatured and renatured before it is ligated to the vector. Induced competent host cells containing activated temperature sensitive T4 endonuclease VII encoded by SEQ ID NO:1 are then added to the heat denatured, renatured PCR ligation mix. Once the DNA to be transformed has entered the cells that express T4 endonuclease VII, those DNA molecules that contain mutations are cleaved by the active T4 endonuclease VII whereas those DNA molecules that are mutation free are not digested by endonuclease VII. Since these host cells will eventually die due to the lethality of T4 endonuclease VII, the non mutant DNAs are rescued In a first preferred embodiment, the host cells are infected with a f1 helper phage that encodes the enzymes necessary to replicate plasmids containing a f1 origin or replication such as pUC and pBluescript and the like. This replication is followed by packaging of a single stranded molecule that can then infect a secondary host strain that harbors the F' episome Incoming DNA molecules that harbor mutations and are cleaved by T4 endonuclease VII are unable to be packaged. In another embodiment, non-mutant plasmids are rescued by conjugal mating. In this scenario, the incoming plasmid DNA molecule should contain an origin of conjugal transfer (oriT; Ditta, G. et. al., *Proc. Natl. Acad. Sci. USA* 77:7347–51, 1980; Hengen, P. N. and V. N. Iyer, *Biotechniques* 13:56–62 (1992)) and a second expression plasmid encoding the conjugal transfer proteins.

Conditional Activity

In one embodiment, the activity of the enzyme is inhibited by heat (e.g., by exposure to temperatures if 37–39° C.). In such an embodiment, the enzyme has a mutation that causes the protein to fold incorrectly at the warmer temperatures, resulting in an inhibition of the enzyme's activity. Upon exposure to cooler temperatures, the protein re-folds correctly, and is active.

Enzymes bind and/or cleave mismatched nucleic acids, and which exhibit conditional activity/inactivity can be used in the present invention. For instance, an enzyme which is active at warmer temperatures, but is inactive at colder temperatures, can be used.

Other inhibition and repression systems can also be used. For instance, enzymes the activity of which are dependent on particular ionic conditions or a particular pH can be used in the invention.

In another embodiment of the invention, the activity of the enzyme is dependent on the availability of an inducer, e.g., a sugar, and amino acid, or other matabolite or compound.

The enzyme can also be controlled by a regulatory nucleic acid. For instance, a promoter that is activated by cold, by heat, ionic concentrations, pH levels, UV irradiation, EMS (ethylmethanesulfonate) damage, or other conditions. For instance, in the λC1 repressor and λ promoter system, the promoter is only active under elevated temperatures.

Activity Levels

If the enzyme used in the invention is highly active, or exhibits some non-specific cleavage (i.e., cleavage at homoduplex, as well as heteroduplex sites), then it is desirable that the control of the enzyme's activity be complete, that is, that repression is complete when the enzyme is exposed to inhibitory conditions. If the enzyme is not highly active, or if the enzyme is very specific in its activity, then one can use an enzyme that is not completely inhibited under the inhibitory conditions.

For instance, T4 endonuclease VII is very highly active, and even a small amount of active enzyme (i.e., as would be found under a "leaky" regulatory system) is lethal to the host *E. coli* cell. On the other hand, T7 endonuclease I exhibits a lower activity, and is not lethal to the host cell when repression of the enzyme is not compete.

Assays

To assay the effectiveness of the methods described herein, and to verify that one has selectively cloned homoduplex nucleic acid molecules, certain control assays can be used.

In one assay, two different restriction fragments are used as controls to form hetero- and homoduplexes. One is a double-stranded restriction fragment containing a nucleic acid sequence (SEQ ID NO:5; FIG. 5) encoding a Green Fluorescent Protein (GFP) (SEQ ID NO:6; FIG. 5), and the other is a restriction fragment that contains a nucleic acid sequence (SEQ ID NO:7; FIG. 6) encoding a mutant Green Fluorescent Protein (G$^m$FP) (SEQ ID NO:8; FIG. 6), which contains a premature stop codon. The normal GFP, when cloned into and expressed constitutively in a host cell, results in the cell fluorescing green under ultraviolet light. A host cell expressing the mutant GFP protein does not fluoresce, i.e., it is white, rather than green.

The two restriction fragments are mixed together, e.g., in a 9:1 ratio (nine parts of GFP-encoding restriction fragment to one part mutant GFP-encoding restriction fragment). The mixture is denatured, renatured, ligated into a vector, and transformed into a host cell of the invention, e.g., a host cell expressing a conditionally-active T4 endonuclease VII. As an additional control, the mixture can also be transformed into a wild type cell, e.g., a host cell not expressing a conditionally-active T4 endonuclease VII. The host cells are then placed under conditions to allow the conditionally-expressed T4 endonuclease VII to act on any heteroduplexes that might be present.

The wild type cells not expressing the enzyme will express the normal GFP and the mutant GFP, and will fluoresce green at a ratio of nine green cells to one non-fluorescent cell. In the cells expressing the conditionally active T4 endonuclease VII, the cells containing homoduplexes of the normal GFP nucleic acid sequence will be present at a rate of the square of the input ratio over one, in this case, 81:1, or $9^2$:1.

For a given starting ratio of X:1 of the two fragments, therefore, host cells not expressing the T4 endonuclease VII will exhibit a ratio of X:1, while host cells expressing the T4 endonuclease VII will exhibit a ratio of $X^2$:1. It is therefore preferable to use the normal GFP at an excess relative to the mutant GFP, as it will be much simpler to determine the difference between ratios of fluorescing cells of 9:1 vs. 81:1 (from a starting ratio of 9:1 normal vs. mutant GFP), than it would be to determine the difference between ratios of 2:1 and 4:1 (from a starting ratio of 2:1 normal vs. mutant GFP).

Other assays, using other fluorescent or otherwise detectable expression products, can also be used.

Kits

The invention is intended to provide novel compositions and methods for the cloning of PCR amplification products devoid of PCR-induced mutations, as described herein. The invention herein also contemplates a kit format that comprises a package unit having one or more containers of the subject composition and in some embodiments including containers of various reagents used for polynucleotide synthesis, including synthesis in PCR. The kit may also contain one or more of the following items: polymerization enzymes, dNTPs, primers, buffers, antibiotics, helper phage, instructions, and controls. The kits may include containers of reagents mixed together in suitable proportions for performing the methods in accordance with the invention.

Reagent containers preferably contain reagents in unit quantities that obviate measuring steps when performing the subject methods. In one embodiment, the kit contains XL1-Blue MRF cells containing a pCALnEK plasmid that expresses the lactose high affinity repressor (lacI$^q$), a second expression plasmid (R6K) that enhances the repression and pACYC 184 expression plasmid containing SEQ ID NO:1, which encodes the temperature sensitive T4 endonuclease VII.

EXAMPLES

Example 1

Preparation of Plasmid Ligation Mixture.

The amplified PCR product of interest is separated from the PCR amplification enzyme by any conventional method (i.e., resin or spin cup to remove enzyme).

The DNA is then heated to 95° C. for 5 minutes, then allowed to slowly cool at room temperature (or in a thermal heating block whose temperature can be ramped down) until the mixture reaches room temperature. This material is then ligated or annealed to the plasmid of interest. This DNA can also be transformed directly into a host cell, depending on the application and the ultimate goal of the experiment. For instance, the transforming DNA can be recombined with a plasmid that is already present in the host, the DNA may recombine with the chromosomal DNA, the DNA may replicate as a linear molecule, etc.

Example 2

Preparation of Host Cells.

The *E. coli* host cells harboring the T4 Endonuclease VII (and the lacI$^q$ encoding repressor plasmid, the lacI$^q$ enhancer plasmid and the F' episome) are grown at 37° C. or above until the cells reach an optical density of 0.2 (at 550 nm). The inducer molecule (IPTG) is added and the cells are maintained at 42° C. for 30 minutes. The cells are rapidly brought to room temperature and are maintained there for a period of 0–3 hours. These cells are then made competent by standard methods (chemically competent or electrocompetent) and frozen at −80° C. prior to use.

These "competent" cells are then thawed, an appropriate volume withdrawn and the plasmid ligation mixture added. Transformation protocol is standard. After heat pulse or electric shock, f1 helper phage (containing the enzymes necessary to replicate and package plasmid DNA molecules containing the f1 phage origin of replication) is added at the same time as the terminal acceptor strain (any *E. coli* containing the F' episome required for f1 infection). The f1 helper phage will package any plasmid DNA molecule containing the f1 origin of replication—those that have been subject to T4 endonuclease VII will not be contiguous and cannot be packaged. The packaged phagemid is then readily transferred to the terminal host.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A kit comprising an isolated DNA encoding the temperature sensitive mutant of bacteriophage T4 Endonuclease VII of SEQ ID NO:2 and packaging materials therefore.

2. A kit comprising an expression vector encoding the temperature sensitive mutant of bacteriophage T4 Endonuclease VII of SEQ ID NO:2 and packaging materials therefore.

3. An isolated nucleic acid encoding a temperature sensitive mutant of bacteriophage T4 Endonuclease VII, wherein said isolated nucleic acid comprises the nucleic acid sequence of SEQ ID NO:1.

4. The isolated nucleic acid of claim 3, wherein said isolated nucleic acid is cloned into an expression vector.

* * * * *

SEQUENCE LISTING

<160> NUMBER OF SEQ ID NOS: 8

<210> SEQ ID NO 1
<211> LENGTH: 473
<212> TYPE: DNA
<213> ORGANISM: Bacteriophage T4
<220> FEATURE:
<221> NAME/KEY: CDS
<222> LOCATION: (1)..(465)
<223> OTHER INFORMATION: Temperature Sensitive mutant T4 endonuclease VII

<400> SEQUENCE: 1

```
atg tta ttg act ggc aaa tta tac aaa gaa gaa aaa cag aaa ttt tat      48
Met Leu Leu Thr Gly Lys Leu Tyr Lys Glu Glu Lys Gln Lys Phe Tyr
1               5                   10                  15 gat gca caa aac ggt aaa tgc tta att tgc caa cga gaa cta aat cct      96
Asp Ala Gln Asn Gly Lys Cys Leu Ile Cys Gln Arg Glu Leu Asn Pro
            20                  25                  30 gat gtt caa gct aat cac ctc gac cat gac cat gaa tta aat gga cca     144
Asp Val Gln Ala Asn His Leu Asp His Asp His Glu Leu Asn Gly Pro
        35                  40                  45 aaa gca gga aag gtg cgt gga ttg ctt tgt aat cta tgc aat gct gca     192
Lys Ala Gly Lys Val Arg Gly Leu Leu Cys Asn Leu Cys Asn Ala Ala
 50                  55                  60 gaa ggt caa atg aag cat aaa ttt aat cgt tct ggc tta aag gga caa     240
Glu Gly Gln Met Lys His Lys Phe Asn Arg Ser Gly Leu Lys Gly Gln
65                  70                  75                  80 ggt gtt gat tat ctt gaa tgg tta gaa aat tta ctt act tat tta aaa     288
Gly Val Asp Tyr Leu Glu Trp Leu Glu Asn Leu Leu Thr Tyr Leu Lys
                85                  90                  95 tcc gat tac acc caa aat aat att cac cct aac ttt gtt gga gat aaa     336
Ser Asp Tyr Thr Gln Asn Asn Ile His Pro Asn Phe Val Gly Asp Lys
            100                 105                 110 tca aag gaa ttt tct cgt tta gga aaa gag gaa atg atg gcc gag atg     384
Ser Lys Glu Phe Ser Arg Leu Gly Lys Glu Glu Met Met Ala Glu Met
        115                 120                 125 ctt caa aga gga ttt gaa tat aat gaa tct gac acc aaa aca caa tta     432
Leu Gln Arg Gly Phe Glu Tyr Asn Glu Ser Asp Thr Lys Thr Gln Leu
    130                 135                 140 ata gct tca ttc aag aag cag ctt aga aga gtt taaaatga                473
Ile Ala Ser Phe Lys Lys Gln Leu Arg Arg Val
145                 150                 155
```

<210> SEQ ID NO 2
<211> LENGTH: 155
<212> TYPE: PRT
<213> ORGANISM: Bacteriophage T4

<400> SEQUENCE: 2

```
Met Leu Leu Thr Gly Lys Leu Tyr Lys Glu Glu Lys Gln Lys Phe Tyr
1               5                   10                  15

Asp Ala Gln Asn Gly Lys Cys Leu Ile Cys Gln Arg Glu Leu Asn Pro
            20                  25                  30

Asp Val Gln Ala Asn His Leu Asp His Asp His Glu Leu Asn Gly Pro
        35                  40                  45

Lys Ala Gly Lys Val Arg Gly Leu Leu Cys Asn Leu Cys Asn Ala Ala
 50                  55                  60

Glu Gly Gln Met Lys His Lys Phe Asn Arg Ser Gly Leu Lys Gly Gln
65                  70                  75                  80
```

```
Gly Val Asp Tyr Leu Glu Trp Leu Glu Asn Leu Leu Thr Tyr Leu Lys
            85                  90                  95

Ser Asp Tyr Thr Gln Asn Asn Ile His Pro Asn Phe Val Gly Asp Lys
            100                 105                 110

Ser Lys Glu Phe Ser Arg Leu Gly Lys Glu Glu Met Met Ala Glu Met
        115                 120                 125

Leu Gln Arg Gly Phe Glu Tyr Asn Glu Ser Asp Thr Lys Thr Gln Leu
        130                 135                 140

Ile Ala Ser Phe Lys Lys Gln Leu Arg Arg Val
145                 150                 155

<210> SEQ ID NO 3
<211> LENGTH: 474
<212> TYPE: DNA
<213> ORGANISM: Bacteriophage T4
<220> FEATURE:
<221> NAME/KEY: CDS
<222> LOCATION: (1)..(471)
<223> OTHER INFORMATION: Wild Type T4 endonuclease VII

<400> SEQUENCE: 3 atg tta ttg act ggc aaa tta tac aaa gaa gaa aaa cag aaa ttt tat       48
Met Leu Leu Thr Gly Lys Leu Tyr Lys Glu Glu Lys Gln Lys Phe Tyr
1               5                   10                  15 gat gca caa aac ggt aaa tgc tta att tgc caa cga gaa cta aat cct       96
Asp Ala Gln Asn Gly Lys Cys Leu Ile Cys Gln Arg Glu Leu Asn Pro
            20                  25                  30 gat gtt caa gct aat cac ctc gac cat gac cat gaa tta aat gga cca      144
Asp Val Gln Ala Asn His Leu Asp His Asp His Glu Leu Asn Gly Pro
        35                  40                  45 aaa gca gga aag gtg cgt gga ttg ctt tgt aat cta tgc aat gct gca      192
Lys Ala Gly Lys Val Arg Gly Leu Leu Cys Asn Leu Cys Asn Ala Ala
    50                  55                  60 gaa ggt caa atg aag cat aaa ttt aat cgt tct ggc tta aag gga caa      240
Glu Gly Gln Met Lys His Lys Phe Asn Arg Ser Gly Leu Lys Gly Gln
65                  70                  75                  80 ggt gtt gat tat ctt gaa tgg tta gaa aat tta ctt act tat tta aaa      288
Gly Val Asp Tyr Leu Glu Trp Leu Glu Asn Leu Leu Thr Tyr Leu Lys
            85                  90                  95 tcc gat tac acc caa aat aat att cac cct aac ttt gtt gga gat aaa      336
Ser Asp Tyr Thr Gln Asn Asn Ile His Pro Asn Phe Val Gly Asp Lys
            100                 105                 110 tca aag gaa ttt tct cgt tta gga aaa gag gaa atg atg gcc gag atg      384
Ser Lys Glu Phe Ser Arg Leu Gly Lys Glu Glu Met Met Ala Glu Met
        115                 120                 125 ctt caa aga gga ttt gaa tat aat gaa tct gac acc aaa aca caa tta      432
Leu Gln Arg Gly Phe Glu Tyr Asn Glu Ser Asp Thr Lys Thr Gln Leu
        130                 135                 140 ata gct tca ttc aag aag cag ctt aga aag agt tta aaa tga             474
Ile Ala Ser Phe Lys Lys Gln Leu Arg Lys Ser Leu Lys
145                 150                 155

<210> SEQ ID NO 4
<211> LENGTH: 157
<212> TYPE: PRT
<213> ORGANISM: Bacteriophage T4

<400> SEQUENCE: 4

Met Leu Leu Thr Gly Lys Leu Tyr Lys Glu Glu Lys Gln Lys Phe Tyr
1               5                   10                  15
```

```
                Asp Ala Gln Asn Gly Lys Cys Leu Ile Cys Gln Arg Glu Leu Asn Pro
                             20                  25                  30

Asp Val Gln Ala Asn His Leu Asp His Asp His Glu Leu Asn Gly Pro
                         35                  40                  45

Lys Ala Gly Lys Val Arg Gly Leu Leu Cys Asn Leu Cys Asn Ala Ala
                     50                  55                  60

Glu Gly Gln Met Lys His Lys Phe Asn Arg Ser Gly Leu Lys Gly Gln
                 65                  70                  75                  80

Gly Val Asp Tyr Leu Glu Trp Leu Glu Asn Leu Leu Thr Tyr Leu Lys
                                 85                  90                  95

Ser Asp Tyr Thr Gln Asn Asn Ile His Pro Asn Phe Val Gly Asp Lys
                                100                 105                 110

Ser Lys Glu Phe Ser Arg Leu Gly Lys Glu Glu Met Met Ala Glu Met
                            115                 120                 125

Leu Gln Arg Gly Phe Glu Tyr Asn Glu Ser Asp Thr Lys Thr Gln Leu
                130                 135                 140

Ile Ala Ser Phe Lys Lys Gln Leu Arg Lys Ser Leu Lys
                145                 150                 155

<210> SEQ ID NO 5
<211> LENGTH: 709
<212> TYPE: DNA
<213> ORGANISM: Aequorea victoria
<220> FEATURE:
<221> NAME/KEY: CDS
<222> LOCATION: (1)..(708)
<223> OTHER INFORMATION: Green Fluorescent Protein

<400> SEQUENCE: 5 aaa gga gaa gaa ctt ttc act gga gtt gtc cca att ctt gtt gaa tta      48
Lys Gly Glu Glu Leu Phe Thr Gly Val Val Pro Ile Leu Val Glu Leu
  1               5                  10                  15 gat ggc gat gtt aat ggg caa aaa ttc tct gtc agt gga gag ggt gaa      96
Asp Gly Asp Val Asn Gly Gln Lys Phe Ser Val Ser Gly Glu Gly Glu
             20                  25                  30 ggt gat gca aca tac gga aaa ctt acc ctt aaa ttt att tgc act act     144
Gly Asp Ala Thr Tyr Gly Lys Leu Thr Leu Lys Phe Ile Cys Thr Thr
         35                  40                  45 ggg aag cta cct gtt cca tgg cca aca ctt gtc act act ttc tct tat     192
Gly Lys Leu Pro Val Pro Trp Pro Thr Leu Val Thr Thr Phe Ser Tyr
     50                  55                  60 ggt gtt caa tgc ttt tca aga tac cca gat cat atg aaa cgg cat gac     240
Gly Val Gln Cys Phe Ser Arg Tyr Pro Asp His Met Lys Arg His Asp
 65                  70                  75                  80 ttt ttc aag agt gcc atg ccc gaa ggt tat gta cag gaa aga act ata     288
Phe Phe Lys Ser Ala Met Pro Glu Gly Tyr Val Gln Glu Arg Thr Ile
                 85                  90                  95 ttt tac aaa gat gac ggg aac tac aag aca cgt gct gaa gtc aag ttt     336
Phe Tyr Lys Asp Asp Gly Asn Tyr Lys Thr Arg Ala Glu Val Lys Phe
            100                 105                 110 gaa ggt gat acc ctt gtt aat aga atc gag tta aaa ggt att gat ttt     384
Glu Gly Asp Thr Leu Val Asn Arg Ile Glu Leu Lys Gly Ile Asp Phe
        115                 120                 125 aaa gaa gat gga aac att ctt gga cac aaa atg gaa tac aac tat aac     432
Lys Glu Asp Gly Asn Ile Leu Gly His Lys Met Glu Tyr Asn Tyr Asn
130                 135                 140 tca cat aat gta tac atc atg gca gac aaa cca aag aat gga atc aaa     480
Ser His Asn Val Tyr Ile Met Ala Asp Lys Pro Lys Asn Gly Ile Lys
145                 150                 155                 160
```

```
gtt aac ttc aaa att aga cac aac att aaa gat gga agc gtt caa tta      528
Val Asn Phe Lys Ile Arg His Asn Ile Lys Asp Gly Ser Val Gln Leu
            165                 170                 175 gca gac cat tat caa caa aat act cca att ggc gat ggc cct gtc ctt      576
Ala Asp His Tyr Gln Gln Asn Thr Pro Ile Gly Asp Gly Pro Val Leu
        180                 185                 190 tta cca gac aac cat tac ctg tcc aca caa tct gcc ctt tcc aaa gat      624
Leu Pro Asp Asn His Tyr Leu Ser Thr Gln Ser Ala Leu Ser Lys Asp
    195                 200                 205 ccc aac gaa aag aga gat cac atg atc ctt ctt gag ttt gta aca gct      672
Pro Asn Glu Lys Arg Asp His Met Ile Leu Leu Glu Phe Val Thr Ala
210                 215                 220 gct ggg att aca cat ggc atg gat gaa cta tac aaa t                    709
Ala Gly Ile Thr His Gly Met Asp Glu Leu Tyr Lys
225                 230                 235
```

<210> SEQ ID NO 6
<211> LENGTH: 236
<212> TYPE: PRT
<213> ORGANISM: Aequorea victoria

<400> SEQUENCE: 6

```
Lys Gly Glu Glu Leu Phe Thr Gly Val Val Pro Ile Leu Val Glu Leu
1               5                   10                  15

Asp Gly Asp Val Asn Gly Gln Lys Phe Ser Val Ser Gly Glu Gly Glu
            20                  25                  30

Gly Asp Ala Thr Tyr Gly Lys Leu Thr Leu Lys Phe Ile Cys Thr Thr
        35                  40                  45

Gly Lys Leu Pro Val Pro Trp Pro Thr Leu Val Thr Thr Phe Ser Tyr
    50                  55                  60

Gly Val Gln Cys Phe Ser Arg Tyr Pro Asp His Met Lys Arg His Asp
65                  70                  75                  80

Phe Phe Lys Ser Ala Met Pro Glu Gly Tyr Val Gln Glu Arg Thr Ile
                85                  90                  95

Phe Tyr Lys Asp Asp Gly Asn Tyr Lys Thr Arg Ala Glu Val Lys Phe
            100                 105                 110

Glu Gly Asp Thr Leu Val Asn Arg Ile Glu Leu Lys Gly Ile Asp Phe
        115                 120                 125

Lys Glu Asp Gly Asn Ile Leu Gly His Lys Met Glu Tyr Asn Tyr Asn
    130                 135                 140

Ser His Asn Val Tyr Ile Met Ala Asp Lys Pro Lys Asn Gly Ile Lys
145                 150                 155                 160

Val Asn Phe Lys Ile Arg His Asn Ile Lys Asp Gly Ser Val Gln Leu
                165                 170                 175

Ala Asp His Tyr Gln Gln Asn Thr Pro Ile Gly Asp Gly Pro Val Leu
            180                 185                 190

Leu Pro Asp Asn His Tyr Leu Ser Thr Gln Ser Ala Leu Ser Lys Asp
        195                 200                 205

Pro Asn Glu Lys Arg Asp His Met Ile Leu Leu Glu Phe Val Thr Ala
    210                 215                 220

Ala Gly Ile Thr His Gly Met Asp Glu Leu Tyr Lys
225                 230                 235
```

<210> SEQ ID NO 7
<211> LENGTH: 709
<212> TYPE: DNA
<213> ORGANISM: Aequorea victoria
<220> FEATURE:

```
<221> NAME/KEY: CDS
<222> LOCATION: (1)..(189)
<223> OTHER INFORMATION: Green Fluorescent Protein mutant protein

<400> SEQUENCE: 7 aaa gga gaa gaa ctt ttc act gga gtt gtc cca att ctt gtt gaa tta        48
Lys Gly Glu Glu Leu Phe Thr Gly Val Val Pro Ile Leu Val Glu Leu
1               5                   10                  15 gat ggc gat gtt aat ggg caa aaa ttc tct gtc agt gga gag ggt gaa        96
Asp Gly Asp Val Asn Gly Gln Lys Phe Ser Val Ser Gly Glu Gly Glu
            20                  25                  30 ggt gat gca aca tac gga aaa ctt acc ctt aaa ttt att tgc act act       144
Gly Asp Ala Thr Tyr Gly Lys Leu Thr Leu Lys Phe Ile Cys Thr Thr
        35                  40                  45 ggg aag cta cct gtt cca tgg cca aca ctt gtc act act tag tga           189
Gly Lys Leu Pro Val Pro Trp Pro Thr Leu Val Thr Thr
    50                  55                  60 tatggtgttc aatgctttc aagataccca gatcatatga aacggcatga cttttcaag       249 agtgccatgc ccgaaggtta tgtacaggaa agaactatat tttacaaaga tgacgggaac     309
tacaagacac gtgctgaagt caagtttgaa ggtgataccc ttgttaatag aatcgagtta     369
aaaggtattg attttaaaga agatggaaac attcttggac acaaaatgga atacaactat     429
aactcacata atgtatacat catggcagac aaaccaaaga atggaatcaa agttaacttc     489
aaaattagac acaacattaa agatggaagc gttcaattag cagaccatta tcaacaaaat     549
actccaattg gcgatggccc tgtccttta ccagacaacc attacctgtc cacacaatct      609
gccctttcca aagatcccaa cgaaaagaga gatcacatga tccttcttga gtttgtaaca     669
gctgctggga ttacacatgg catggatgaa ctatacaaat                           709

<210> SEQ ID NO 8
<211> LENGTH: 61
<212> TYPE: PRT
<213> ORGANISM: Aequorea victoria

<400> SEQUENCE: 8

Lys Gly Glu Glu Leu Phe Thr Gly Val Val Pro Ile Leu Val Glu Leu
1               5                   10                  15

Asp Gly Asp Val Asn Gly Gln Lys Phe Ser Val Ser Gly Glu Gly Glu
            20                  25                  30

Gly Asp Ala Thr Tyr Gly Lys Leu Thr Leu Lys Phe Ile Cys Thr Thr
        35                  40                  45

Gly Lys Leu Pro Val Pro Trp Pro Thr Leu Val Thr Thr
    50                  55                  60
```